United States Patent [19]
Moriguchi et al.

[11] Patent Number: 5,962,480
[45] Date of Patent: Oct. 5, 1999

[54] DRUG FOR AMELIORATING BRAIN DISEASES

[75] Inventors: Toru Moriguchi; Hiromichi Matsuura, both of Takata-gun; Hiroshi Saito, Tokyo, all of Japan

[73] Assignee: Wakunaga Pharmaceutical Co., Ltd., Osaka, Japan

[21] Appl. No.: 08/981,496

[22] PCT Filed: Jul. 11, 1996

[86] PCT No.: PCT/JP96/01935

§ 371 Date: Jan. 9, 1998

§ 102(e) Date: Jan. 9, 1998

[87] PCT Pub. No.: WO97/02822

PCT Pub. Date: Jan. 30, 1997

[30] Foreign Application Priority Data

Jul. 12, 1995 [JP] Japan .................................... 7-175711

[51] Int. Cl.$^6$ .......................... A61K 31/44; A61K 31/35
[52] U.S. Cl. ........................................... 514/350; 514/460
[58] Field of Search ..................... 514/460, 350

[56] References Cited

PUBLICATIONS

Database Chemical Abstracts on STN, Kodera et al, AN 1990:73738, "Allixin, a stress compound from garlic", Chem. Pharm. Bull. (1989), 37(6), 1656–8, Jan. 1990.
Database CHemical Abtracts on STN, AN 1990:191529, Nishino et al, "Antitumor–promoting activity of allixin . . . ", Cancer J. (Jan. 1990), 3(1), 20–1.
Database Chemical Abstracts on STN, Yamasaki et al, AN 1991:574254, "Effect of Allixin, a phytoalxin produced by garlic, on mutagenesis, DNA–binging and metabolism of aflatoxin B1", Cancer Lett. (Shannon, Irel.) (Jan. 1991), 59(2), 89–94.
Database Chemical Abstracts on STN, AN 1983:124508, "Hydroxypyranones as antioxidants for oils and fats", Jpn. Kokai Tokkyo Koho, JP 57137394, Aug. 24, 1982.
Database Chemical Abstracts on STN, AN 1992:207843, Yamamoto, "Pharmaceuticals containing allomaltol for treatment of pigmentation disorders", Jpn. Kokai Tokkyo Koho, 5 pp., JP 04036217, Feb. 6, 1992.

*Primary Examiner*—Keith D. MacMillan
*Attorney, Agent, or Firm*—Oblon, Spivak, McClelland, Maier & Neustadt, P.C.

[57] ABSTRACT

The present invention discloses a drug for ameliorating brain diseases which comprises as an active ingredient a compound represented by the following formula (1):

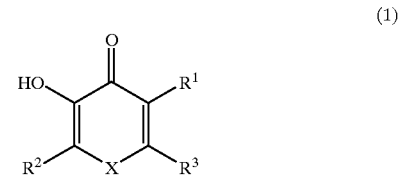

or a salt thereof. Because of inhibiting a decrease in brain neurons and promoting branching of neurites, this drug is efficacious in the prevention and treatment of dementia, etc. in association with degeneration and sloughing of brain neurons.

21 Claims, 2 Drawing Sheets

DRUG FOR AMELIORATING BRAIN DISEASES

TECHNICAL FIELD

The present invention relates to a drug for ameliorating brain diseases, and more particularly to a drug for ameliorating brain diseases useful for the prevention and treatment of cerebral function disorders, such as dementia, caused by degeneration and sloughing of brain neurons.

BACKGROUND ART

In recent years, among intrinsic diseases that occur as age increases, brain diseases led by Alzheimer's disease have come to be great social problems. The human brain contains several tens of billions of neurons. The terminal portions of neurites of the neurons transmit information from one to another at junctional portions called synapses by the mediation of a neurotransmitter, forming complicated neurological circuits. Almost all brain disorders are considered to be caused by the destruction of neurological circuits due to degeneration or sloughing of neurons. As is widely accepted, neurons that have matured can no longer undergo cell division. Therefore, needless to say, damage to neurons considerably affects maintenance of brain functions.

Recently, substances that participate in differentiation and growth of nerve tissue have been searched for in the living body, and several in vivo hormones have already been clarified to be active substances.

However, it has been pointed out that these hormones disturb the in vivo hormone balance when used at a concentration where they exhibits their activity on neurons, and therefore in actual use they are problematic for administration. In view of the foregoing, there is a strong need for the development of extracorporeally derived pharmaceuticals that are effective in the prevention of damage to neurons, particularly prevention or treatment of degeneration and sloughing of neurons.

Accordingly, the object of the present invention is to provide a drug for treating brain diseases, which drug enables prevention or treatment of dementia and similar diseases caused by degeneration or sloughing of neurons.

DISCLOSURE OF THE INVENTION

The present inventors have conducted a screening of a wide variety of compounds originating from plants, and have discovered that a compound having a gamma-pyrone ring—which is known to be so-called stress compounds produced when garlic undergoes certain stress—and their analogs inhibit decrease in brain neurons and promote branching of neurites, and therefore are useful as drugs for ameliorating brain diseases such as dementia caused in association with degeneration and sloughing of brain neurons. The present invention has been accomplished based on this finding.

Specifically, the present invention provides a compound for ameliorating brain diseases comprising as the active ingredient a compound represented by the following formula (1):

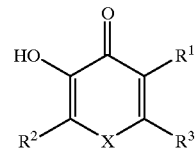

(1)

[wherein $R^1$ represents a hydrogen atom, a hydroxyl group, a lower alkoxyl group, or a lower alkyl group; each of $R^2$ and $R^3$ represents a hydrogen atom, a lower alkyl group, a substituted lower alkyl group, a lower alkenyl group, a phenyl group, a substituted phenyl group, a styryl group, or a substituted styryl group; and X represents an oxygen atom or a nitrogen atom which may be substituted by a lower alkyl group] or a salt thereof.

The present invention also provides a composition for ameliorating brain diseases, which composition contains a compound represented by the above formula (1) or a salt thereof and a pharmaceutically acceptable carrier.

The present invention also provides use, in the manufacture of a therapeutic drug of brain diseases, of a compound represented by the above formula (1) or a salt thereof.

The present invention also provides a method for ameliorating brain diseases, characterized by administering to a patient an effective amount of the compound of formula (1) or a salt thereof.

BEST MODE FOR CARRYING OUT THE INVENTION

Figure 1:
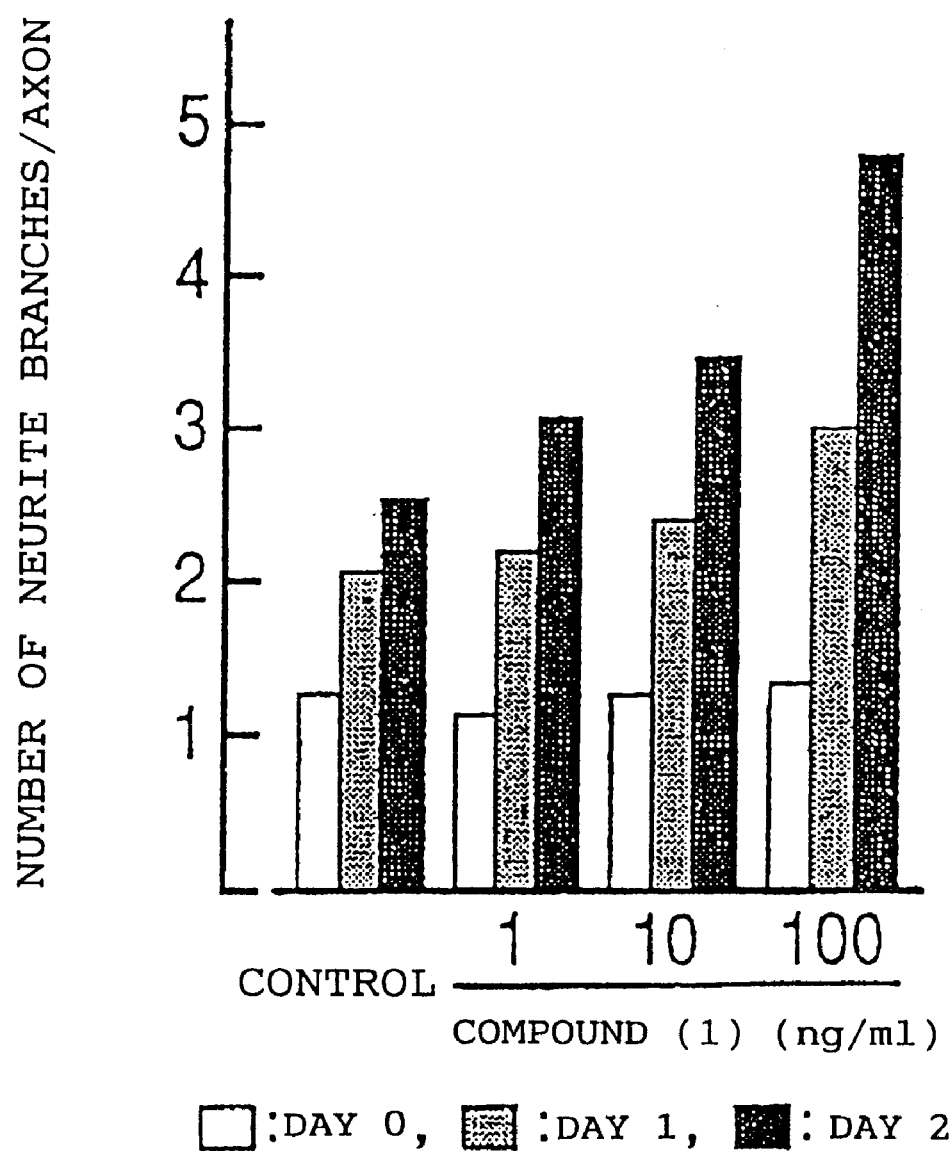
FIG. 1 shows the branching promotion effect of compound (1) on neurites.

The active ingredient of the drug of the present invention for ameliorating brain diseases is a compound represented by the above-described formula (1) or a salt thereof. In the above-described formula (1), examples of the lower alkyl group include linear or branched C1–C6 alkyl groups. Specifically, mention may be given of a methyl group, an ethyl group, a n-propyl group, an isopropyl group, a n-butyl group, an isobutyl group, a sec-butyl group, a tert-butyl group, a n-pentyl group, and a n-hexyl group. Examples of the lower alkenyl group include linear or branched C2–C6 alkenyl groups. Specifically, mention may be given of a vinyl group, an allyl group, a butenyl group, and a pentenyl group. Examples of the substituted phenyl group include phenyl groups each having, on the ring, one to three hydroxyl groups, amino groups, or lower alkyl groups. Examples of the lower alkoxyl group include linear or branched C1–C6 alkoxyl groups. Specifically, mention may be given of a methoxy group, an ethoxy group, a n-propoxy group, an isopropoxy group, a n-butoxy group, an isobutoxy group, a sec-butoxy group, a tert-butoxy group, a n-pentoxy group, and a n-hexyloxy group. Examples of the substituted lower alkyl group include lower alkyl groups which have been substituted by one to three hydroxyl groups, amino groups, di-lower alkylamino groups, and halogen atoms. Substituted styryl groups include styryl groups each having, on the benzene ring, one to three hydroxyl groups, amino groups, lower alkyl groups and halogen atoms.

In formula (1), $R^1$ is particularly preferably a hydrogen atom, a hydroxyl group, or a lower alkoxyl group. $R^2$ is particularly preferably a hydrogen atom, a lower alkyl group, a hydroxy lower alkyl group, or a di-lower alkylamino lower alkyl group. $R^3$ is preferably a hydrogen atom, a lower alkyl group, a hydroxy lower alkyl group, or a styryl group.

Compounds of formula (1) may form acid addition salts or base addition salts together with arbitrary acids or bases. The resultant salts are within the scope of the present invention. Examples of acid addition salts include (a) salts formed with mineral acids such as hydrochloric acid and sulfuric acid, (b) salts formed with organic carboxylic acids such as formic acid and citric acid, (c) salts formed with sulfonic acids such as methanesulfonic acid and benzenesulfonic acid. Examples of base addition salts include (a) salts formed with alkali metals such as sodium and potassium, (b) salts formed with alkaline earth metals such as calcium and magnesium, (c) salts formed with nitrogen-containing organic bases such as ammonium and triethylamine.

The compounds of formula (1) and salts thereof may form hydrates.

Specific examples of the compounds of formula (1) used in the present invention include the following:

3-Hydroxy-6-methyl-5-methoxy-2-pentyl-4H-pyran-4-one (hereinafter referred to as Compound (1))

3-Hydroxy-6-methyl-4H-pyran-4-one (hereinafter referred to as Compound (2))

3-Hydroxy-2,6-dimethyl-4H-pyran-4-one (hereinafter referred to as Compound (3))

3-Hydroxy-6-methyl-2-propyl-4H-pyran-4-one (hereinafter referred to as Compound (4))

3-Hydroxy-6-methyl-2-pentyl-4H-pyran-4-one (hereinafter referred to as Compound (5))

3-Hydroxy-6-methyl-2-hydroxymethyl-4H-pyran-4-one (hereinafter referred to as Compound (6))

3-Hydroxy-6-methyl-2-dimethylaminomethyl-4H-pyran-4-one-HCl (hereinafter referred to as Compound (7))

3-Hydroxy-6-hydroxymethyl-4H-pyran-4-one (hereinafter referred to as Compound (8))

3-Hydroxy-6-hydroxymethyl-2-pentyl-4H-pyran-4-one (hereinafter referred to as Compound (9))

3-Hydroxy-6-hydroxymethyl-2-(1'-hydroxypentyl)-4H-pyran-4-one (hereinafter referred to as Compound (10))

3,5-Dihydroxy-6-methyl-2-pentyl-4H-pyran-4-one (hereinafter referred to as Compound (11))

3-Hydroxy-6-styryl-4H-pyran-4-one (hereinafter referred to as Compound (12))

3-Hydroxy-6-methyl-4-pyridone (hereinafter referred to as Compound (13))

3-Hydroxy-6-hydroxymethyl-4-pyridone (hereinafter referred to as Compound (14))

Of all compounds of formula (1), Compound (1) is known as a so-called stress compound which is produced when garlic undergoes certain stress (Chem. Pharm. Bull., 37(6), 1656–1658 (1989)). Compounds other than Compound (1) may also be obtained in accordance with known methods—alkylation, reduction, oxidation, and conversion from an oxygen atom to a nitrogen atom or an alkylated nitrogen atom (Bull. Univ. Osaka Pref., Ser. B. 22, 209–267 (1970); Acta Chemica Scandinavica. 44, 916–926 (1990) and their citations).

As will be described hereinbelow in the "Examples" section, compounds of formula (1) or salts thereof exhibit inhibitory effect against reduction in brain neurons and branching promotion effect on neurites. Therefore, the compounds are useful for the prevention and treatment of brain diseases such as dementia caused by the degeneration and sloughing of brain neurons. Regarding the toxicity of compound (1) of the present invention, in view that 50% lethal death ($LD_{50}$) values with rats and mice in the case of oral administration are not less than 1,000 mg/kg, the formula (1) compounds of the present invention are determined to be low toxic in general.

The drugs of the present invention for treating brain diseases may be in the form of the aforementioned compounds of formula (1) or salts thereof per se, or may be prepared by incorporating the aforementioned compounds (1) or salts thereof into pharmaceutically-acceptable carriers such as a pharmaceutical vehicle, binder, and a diluent. They may be prepared into oral or parenteral preparations of arbitrary physical shapes, including powders, granules, tablets, capsules, syrups, and injections. The dose may vary in accordance with the age, body weight, symptom, etc. In the case of oral administration, the drug of the invention is preferably administered in an amount of 1 mg–5 g, more preferably 10 mg–1 g per day, in terms of the weight of the compounds of formula (1). According to a preferred mode of the present invention, the drug has a unit dosage form allowing administration of the above-mentioned daily dosage at a single time or in divided times. Needless to say, other drugs may also be incorporated.

EXAMPLES

The present invention will next be described in detail by way of examples, which should not be construed as limiting the invention thereto.

Example 1

[Effect of compound (1) to inhibit reduction in survival rate of neurons]

From a rat at the 18th day of pregnancy (having an 18-day old embryo) the uterus was aseptically removed under etherification, and the fetus was obtained. The whole brain was collected from the fetus. From the brain placed in an L-15 medium were removed under a microscope the hippocampus, striate body, septum, cerebral cortex, and cerebellum. They were respectively minced with a knife. The minced tissue was treated by the addition of trypsin (0.25%) and DNase (0.01%) for 30 minutes at 37° C. to thereby isolate cells. The thus-isolated cells were suspended in Eagle's MEM medium supplemented with 10% fetal calf serum, and inoculated at a concentration of $4 \times 10^4$ cells/cm$^2$ into wells of a 48-well plate which had been coated with poly-L-lysin in advance. Following incubation for 24 hours, the medium was replaced by a serum-free DMEM/F-12 medium containing the drug. After three-days' additional incubation (six days for the striate body), the cells were fixed, stained, and the number of surviving cells in each well was counted.

The results regarding compound (1) are shown in Table 1.

TABLE 1

Effect of compound (1) to inhibit reduction in survival rate of neurons

| Test group (g/ml) | Number of surviving cells | | | | |
|---|---|---|---|---|---|
| | Hippo-campus | Septum | Cerebral cortex | Striate body | Cere-bellum |
| Control group | 100.0± 3.2 | 100.0± 2.9 | 100.0± 3.3 | 100.0± 4.8 | 100.0± 14.0 |
| $10^{-9}$ | 108.9± 1.7 | 128.1± 4.0 | 104.3± 8.9 | 125.5± 6.8 | 136.9± 11.8 |
| $10^{-8}$ | 133.9± 4.5 | 150.2± 4.8 | 107.2± 10.5 | 138.7± 3.3 | 136.3± 12.9 |
| $10^{-7}$ | 145.6± 2.1 | 157.3± 5.3 | 125.3± 6.1 | 160.5± 3.8 | 147.2± 6.4 |
| $10^{-6}$ | 57.8± 3.4 | 71.6± 4.1 | 90.2± 7.2 | 83.8± 6.7 | 65.3± 6.1 |

As is apparent from Table 1, in the control group (no drug added), the number of surviving cells among the isolated cells that were inoculated at a concentration of $4 \times 10^4$ cells/cm$^2$ decreased to as low as to $1 \times 10^4$ cells/cm$^2$ on the third day of incubation with the serum-free medium. In contrast, compound (1) exhibited effect of inhibiting reduction of neurons within the concentration range of 1–100 ng/ml in a concentration-dependent manner (activity of control: 100%).

Example 2

[Effect of compounds (2) through (14) to inhibit reduction in survival rate of neurons]

Compounds (2) through (14) were tested analogously to Example 1 using hippocampus cells prepared in a manner similar to Example 1. As structural comparative compounds, the following compounds were used: 4H-pyran-4-one (hereinafter referred as Compound (15) and 3-methoxy-6-hydroxymethyl-4H-pyran-4-one (hereinafter referred to as Compound (16)).

The results are shown in Table 2. The structural comparative compounds (15) and (16) exhibited no inhibitory effect against reduction in survival rate of hippocampus neurons. Therefore, it is required that 3-hydroxy-4H-pyran-4-one be present as an essential backbone structure for the manifestation of activity. Compounds (2) through (12) exhibited inhibitory effect against reduction in survival rate of brain neurons. Moreover, a gamma-pyridone derivative in which the oxygen atom in the gamma-pyrone ring has been substituted by a nitrogen atom was confirmed to have a similar level of inhibitory effect against reduction survival in survival rate of neurons.

TABLE 2

Inhibitory effect of gamma-pyrone derivatives against reduction in survival rate of neurons

| Compound | $10^{-9}$ | $10^{-8}$ | $10^{-7}$ | $10^{-6}$ | $10^{-5}$ (g/ml) |
|---|---|---|---|---|---|
| (2) | ± | ± | ± | ↑ | ↑↑ |
| (3) | ± | ↑ | ↑↑ | ↑↑ | ↑ |
| (4) | ± | ± | ↑ | ± | |
| (5) | ± | ± | ↑ | X | |
| (6) | ± | ± | ↑ | ↑ | ↑ |
| (7) | ± | ± | ± | ↑ | ↑ |
| (8) | ± | ± | ± | ↑ | ↑ |
| (9) | ± | ± | ± | ± | ↑ |
| (10) | ± | ± | ± | ↑ | ↑↑ |

TABLE 2-continued

Inhibitory effect of gamma-pyrone derivatives against reduction in survival rate of neurons

| Compound | $10^{-9}$ | $10^{-8}$ | $10^{-7}$ | $10^{-6}$ | $10^{-5}$ (g/ml) |
|---|---|---|---|---|---|
| (11) | ± | ± | ↑↑ | X | |
| (12) | ± | ± | ↑ | ↑ | X |
| (13) | ± | ± | ± | ↑ | ↑↑ |
| (14) | ± | ± | ± | ± | ↑ |
| (15) | ± | ± | ± | ± | ± |
| (16) | ± | ± | ± | ± | ± |

When the survival rate of the neurons in the control group was taken as 100%:
X: Not more than 90%±: 90~110% ↑: 110 ~130%
↑↑: 130~150%o.

Example 3

[Branching promotion effect on neurites]

The hippocampus cells obtained in a manner similar to that in Example 1 were incubated for 24 hours in a medium containing fetal calf serum, then for a further 24 hours in a serum-free medium. Subsequently, the drug was added. When one day and two days elapsed after addition of the drug, photographs were taken of the same cells. The number of branches from the longest neurite was counted.

Figure 2:
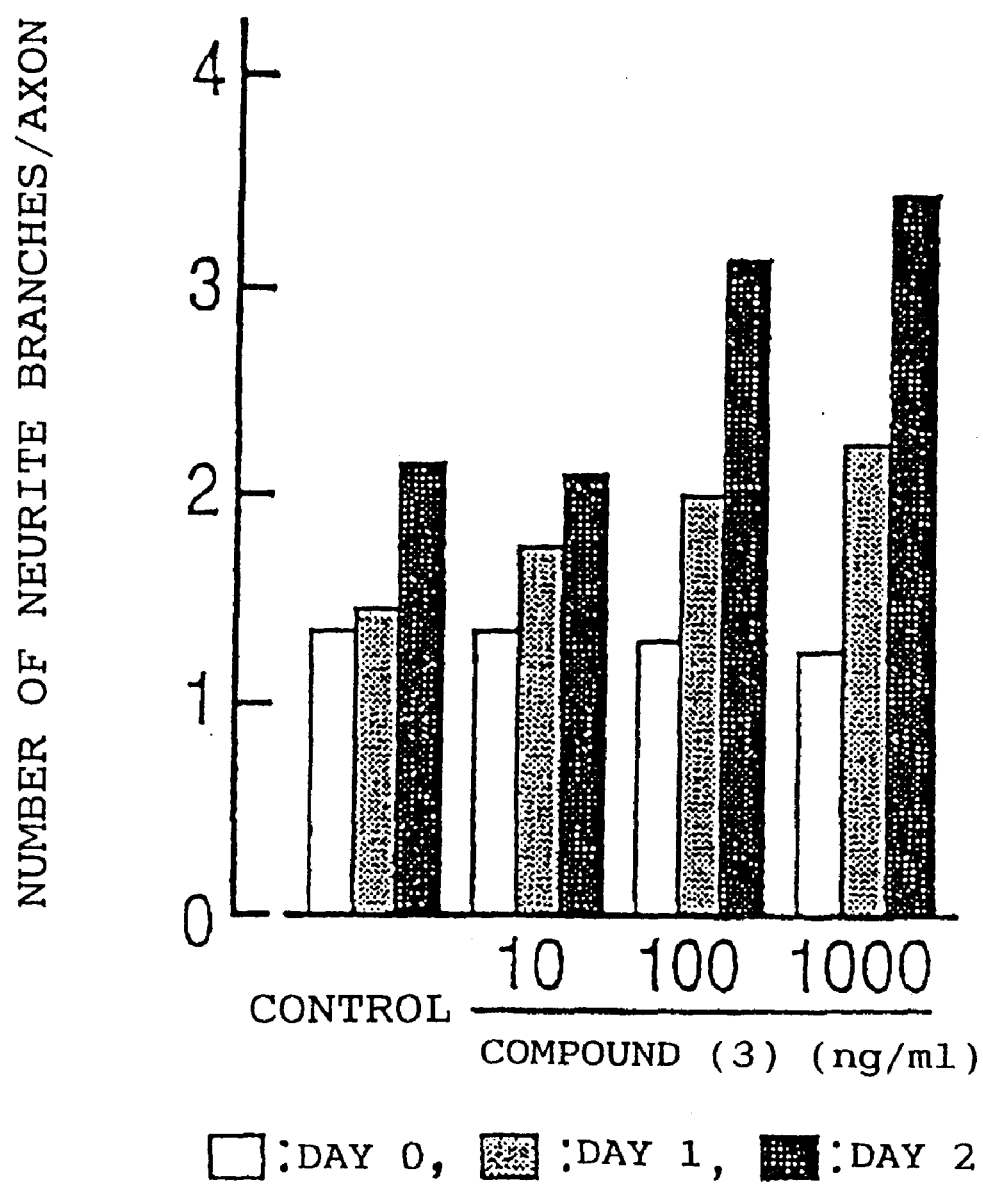
FIG. 2 shows the branching promotion effect of compound (3) on neurites.

The results are shown in FIGS. 1 and 2. Compounds (1) and (3) were confirmed to have a branching promotion effect on neurites.

Industrial Applicability

The drug of the present invention for ameliorating brain diseases, inhibiting reduction of brain neurons and promoting branching of neurites, is useful for the prevention and treatment of brain diseases such as dementia in association with degeneration and sloughing of brain neurons.

We claim:

1. A method for ameliorating brain disease caused by degeneration and sloughing of brain neurons, comprising administering to a patient in need thereof an effective amount of a compound represented by formula (1):

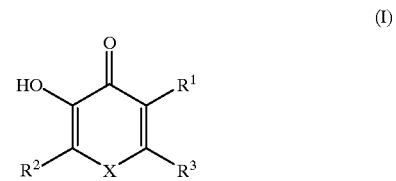

(I)

wherein
R$^1$ represents a hydrogen atom, a hydroxyl group, a lower alkoxyl group, or a lower alkyl group;
R$^2$ and R$^3$ each, independently, represent a hydrogen atom, a lower alkyl group, a lower alkyl group substituted by one to three substituents selected from the group consisting of a hydroxyl group, an amino group, a di-lower alkylamino group and a halogen atom, a lower alkenyl group, a phenyl group, a phenyl group substituted by one to three substituents selected from the group consisting of a hydroxyl group, an amino group and a lower alkyl group, a styryl group, or a styryl group substituted by one to three substituents selected from the group consisting of a hydroxyl group, an amino group, a lower alkyl group and a halogen atom; and X represents an oxygen atom or a nitrogen atom, wherein the nitrogen atom is unsubstituted or substituted by a lower alkyl group, or a salt thereof.

2. The method of claim 1, wherein $R^1$ represents a hydrogen atom, a hydroxyl group, or a lower alkoxyl group;

$R^2$ represents a hydrogen atom, a lower alkyl group, or a lower alkyl group substituted by one to three substituents selected from the group consisting of a hydroxyl group and a di-lower alkylamino group; and $R^3$ represents a hydrogen atom, a lower alkyl group, a lower alkyl group substituted by one to three hydroxyl groups, or a styryl group, or a salt thereof.

3. The method of claim 1, wherein the compound represented by formula (1), or a salt thereof, is administered in combination with a pharmaceutically acceptable carrier.

4. The method of claim 1, wherein the compound represented by formula (1) is 3-hydroxy-6-methyl-5-methoxy-2-pentyl-4H-pyran-4-one, 3-hydroxy-6-methyl-4H-pyran-4-one, 3-hydroxy-2,6-dimethyl-4H-pyran-4-one, 3-hydroxy-6-methyl-2-propyl-4H-pyran-4-one, 3-hydroxy-6-methyl-2-pentyl-4H-pyran-4-one, 3-hydroxy-6-methyl-2-hydroxymethyl-4H-pyran-4-one, 3-hydroxy-6-methyl-2-dimethylaminomethyl-4H-pyran-4-one.HCl 3-hydroxy-6-hydroxymethyl-4H-pyran-4-one, 3-hydroxy-6-hydroxymethyl-2-pentyl-4H-pyran-4-one, 3-hydroxy-6-hydroxymethyl-2-(1'-hydroxypentyl)-4H-pyran-4-one, 3,5-dihydroxy-6-methyl-2-pentyl-4H-pyran-4-one, 3-hydroxy-6-styryl-4H-pyran-4-one, 3-hydroxy-6-methyl-4-pyridone, or 3-hydroxy-6-hydroxymethyl-4-pyridone, or a salt thereof.

5. The method of claim 1, wherein the compound represented by formula (1) is an acid addition salt.

6. The method of claim 1, wherein the compound represented by formula (1) is a base addition salt.

7. The method of claim 1, wherein 1 mg to 5 g of the compound represented by formula (1) is administered to the patient per day.

8. A method of inhibiting reduction in the survival rate of brain neurons, comprising administering to a patient in need thereof an effective amount of a compound represented by formula (1):

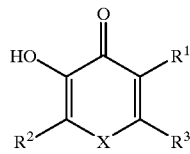

(I)

wherein $R^1$ represents a hydrogen atom, a hydroxyl group, a lower alkoxyl group, or a lower alkyl group;

$R^2$ and $R^3$ each, independently, represent a hydrogen atom, a lower alkyl group, a lower alkyl group substituted by one to three substituents selected from the group consisting of a hydroxyl group, an amino group, a di-lower alkylamino group and a halogen atom, a lower alkenyl group, a phenyl group, a phenyl group substituted by one to three substituents selected from the group consisting of a hydroxyl group, an amino group and a lower alkyl group, a styryl group, or a styryl group substituted by one to three substituents selected from the group consisting of a hydroxyl group, an amino group, a lower alkyl group and a halogen atom; and X represents an oxygen atom or a nitrogen atom, wherein the nitrogen atom is unsubstituted or substituted by a lower alkyl group, or a salt thereof.

9. The method of claim 8, wherein $R^1$ represents a hydrogen atom, a hydroxyl group, or a lower alkoxyl group;

$R^2$ represents a hydrogen atom, a lower alkyl group, or a lower alkyl group substituted by one to three substituents selected from the group consisting of a hydroxyl group and a di-lower alkylamino group; and $R^3$ represents a hydrogen atom, a lower alkyl group, a lower alkyl group substituted by one to three hydroxyl groups, or a styryl group, or a salt thereof.

10. The method of claim 8, wherein the compound represented by formula (1), or a salt thereof, is administered in combination with a pharmaceutically acceptable carrier.

11. The method of claim 8, wherein the compound represented by formula (1) is 3-hydroxy-6-methyl-5-methoxy-2-pentyl-4H-pyran-4-one, 3-hydroxy-6-methyl-4H-pyran-4-one, 3-hydroxy-2,6-dimethyl-4H-pyran-4-one, 3-hydroxy-6-methyl-2-propyl-4H-pyran-4-one, 3-hydroxy-6-methyl-2-pentyl-4H-pyran-4-one, 3-hydroxy-6-methyl-2-hydroxymethyl-4H-pyran-4-one, 3-hydroxy-6-methyl-2-dimethylaminomethyl-4H-pyran-4-one.HCl 3-hydroxy-6-hydroxymethyl-4H-pyran-4-one, 3-hydroxy-6-hydroxymethyl-2-pentyl-4H-pyran-4-one, 3-hydroxy-6-hydroxymethyl-2-(1'-hydroxypentyl)-4H-pyran-4-one, 3,5-dihydroxy-6-methyl-2-pentyl-4H-pyran-4-one, 3-hydroxy-6-styryl-4H-pyran-4-one, 3-hydroxy-6-methyl-4-pyridone, or 3-hydroxy-6-hydroxymethyl-4-pyridone, or a salt thereof.

12. The method of claim 8, wherein the compound represented by formula (1) is an acid addition salt.

13. The method of claim 8, wherein the compound represented by formula (1) is a base addition salt.

14. The method of claim 8, wherein 1 mg to 5 g of the compound represented by formula (1) is administered to the patient per day.

15. A method of promoting branching of neurites, comprising administering to a patient in need thereof an effective amount of a compound represented by formula (1):

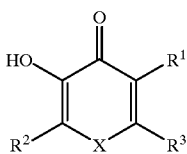

(I)

wherein $R^1$ represents a hydrogen atom, a hydroxyl group, a lower alkoxyl group, or a lower alkyl group;

$R^2$ and $R^3$ each, independently, represent a hydrogen atom, a lower alkyl group, a lower alkyl group substituted by one to three substituents selected from the group consisting of a hydroxyl group, an amino group, a di-lower alkylamino group and a halogen atom, a lower alkenyl group, a phenyl group, a phenyl group substituted by one to three substituents selected from the group consisting of a hydroxyl group, an amino group and a lower alkyl group, a styryl group, or a styryl group substituted by one to three substituents selected from the group consisting of a hydroxyl group, an amino group, a lower alkyl group and a halogen atom; and X represents an oxygen atom or a nitrogen atom, wherein the nitrogen atom is unsubstituted or substituted by a lower alkyl group, or a salt thereof.

16. The method of claim 15, wherein $R^1$ represents a hydrogen atom, a hydroxyl group, or a lower alkoxyl group;

$R^2$ represents a hydrogen atom, a lower alkyl group, or a lower alkyl group substituted by one to three substituents selected from the group consisting of a hydroxyl group and a di-lower alkylamino group; and $R^3$ represents a hydrogen atom, a lower alkyl group, a lower alkyl group substituted by one to three hydroxyl groups, or a styryl group, or a salt thereof.

17. The method of claim 15, wherein the compound represented by formula (1), or a salt thereof, is administered in combination with a pharmaceutically acceptable carrier.

18. The method of claim 15, wherein the compound represented by formula (1) is 3-hydroxy-6-methyl-5-methoxy-2-pentyl-4H-pyran-4-one, 3-hydroxy-6-methyl-4H-pyran-4-one, 3-hydroxy-2,6-dimethyl-4H-pyran-4-one, 3-hydroxy-6-methyl-2-propyl-4H-pyran-4-one, 3-hydroxy-6-methyl-2-pentyl-4H-pyran-4-one, 3-hydroxy-6-methyl-2-hydroxymethyl-4H-pyran-4-one, 3-hydroxy-6-methyl-2-dimethylaminomethyl-4H-pyran-4-one.HCl 3-hydroxy-6-hydroxymethyl-4H-pyran-4-one, 3-hydroxy-6-hydroxymethyl-2-pentyl-4H-pyran-4-one, 3-hydroxy-6-hydroxymethyl-2-(1'-hydroxypentyl)-4H-pyran-4-one, 3,5-dihydroxy-6-methyl-2-pentyl-4H-pyran-4-one, 3-hydroxy-6-styryl-4H-pyran-4-one, 3-hydroxy-6-methyl-4-pyridone, or 3-hydroxy-6-hydroxymethyl-4-pyridone, or a salt thereof.

19. The method of claim 15, wherein the compound represented by formula (1) is an acid addition salt.

20. The method of claim 15, wherein the compound represented by formula (1) is a base addition salt.

21. The method of claim 14, wherein 1 mg to 5 g of the compound represented by formula (1) is administered to the patient per day.

* * * * *